(12) United States Patent
Wardlaw

(10) Patent No.: US 6,287,870 B1
(45) Date of Patent: Sep. 11, 2001

(54) METHOD AND ASSEMBLY FOR SEPARATING FORMED CONSTITUENTS FROM A LIQUID CONSTITUENT IN A COMPLEX BIOLOGIC FLUID SAMPLE

(75) Inventor: Stephen C. Wardlaw, Lyme, CT (US)

(73) Assignee: Robert A. Levine, Guilford, CT (US)

( * ) Notice: Subject to any disclaimer, the term of this patent is extended or adjusted under 35 U.S.C. 154(b) by 0 days.

(21) Appl. No.: 09/366,881

(22) Filed: Aug. 20, 1999

(51) Int. Cl.$^7$ ................................................. G01N 21/00
(52) U.S. Cl. ........................ 436/164; 436/63; 436/165; 436/169; 436/174; 436/180; 422/56; 422/58
(58) Field of Search ............................. 436/63, 164, 165, 436/169, 174, 180; 422/56, 58; 435/173.9; 604/368; 356/36–42, 244–246, 256, 904, 928–930

(56) References Cited

U.S. PATENT DOCUMENTS

| 3,990,849 | * | 11/1976 | Lee et al. | 210/516 |
| 4,250,257 | * | 2/1981 | Lee et al. | 435/4 |
| 5,336,599 | * | 8/1994 | Kitajima | 435/15 |

OTHER PUBLICATIONS

Horbett, T. A. and Hoffman, A. S. "Bovine plasma protein adsorption onto radiation–grafted hydrogels based on hydroxyethyl methacrylate and N–vinylpyrrolidone", Adv. Chem. Ser. (1975), 145(Appl. Chem. Protein Interfaces, Symp., 1973), 230–54.*

Merrill, Edward W.; Pekala, Richard W.; Mahmud, Nargis A. "Hydrogels for blood contact", Hydrogels Med. Pharm. (1987), vol. 3, 1–16.*

* cited by examiner

Primary Examiner—Jill Warden
Assistant Examiner—Yelena Gakh
(74) Attorney, Agent, or Firm—William W. Jones

(57) ABSTRACT

Formed constituents in an aqueous based fluid biologic material sample are separated from the aqueous constituent of the sample, and are concentrated in an examining instrument's focal plane where they can be examined under magnification. Examples of fluids that can be analyzed in this fashion include urine; cerebrospinal fluid; pleural fluid; ascites; fluids aspirated from cysts such as thyroid and breast cysts; cytologic specimens which have been placed in an aqueous fluid; platelet-rich plasma; and the like. The sample is placed in a chamber having a layer of a hydrophilic hydrogel covering a surface of the chamber. An opposite surface of the chamber is transparent, and may be formed by a microscope slide cover slip, or the like. The volume of hydrogel in the chamber is sufficient so that, when the hydrogel absorbs essentially all of the aqueous fraction of the sample, the hydrogel will expand and fill the chamber. The capture surface of the expanded hydrogel is preferably planar, and any formed constituents in the sample will be captured on the capture surface of the hydrogel layer, and will not be absorbed into the hydrogel. Formed constituents, such as: cells; bacteria; crystals; protozoa; ova; parasites; and the like, can be differentially highlighted by use of labeled antibodies, selective stains, or the like, so as to enable optical examination and differentiation of various formed constituents which may be in the sample. Formed constituents may be harvested from the capture surface of the expanded hydrogel layer for more detailed examination and analysis. The capture surface of the hydrogel may be provided with a plurality of beads for use in locating the capture surface with an optical scanning instrument, and for re-establishing previously scanned fields of view.

6 Claims, 1 Drawing Sheet

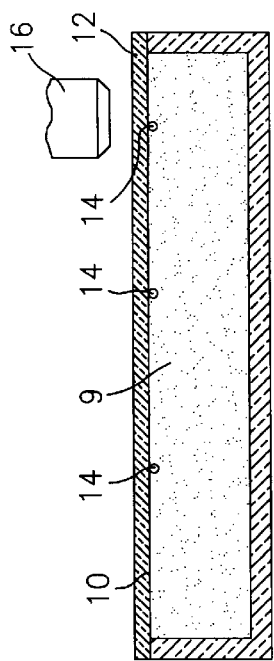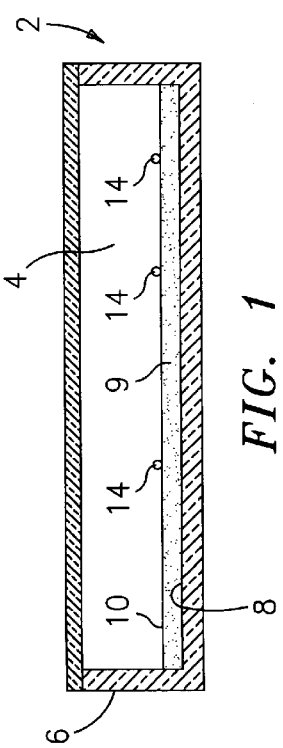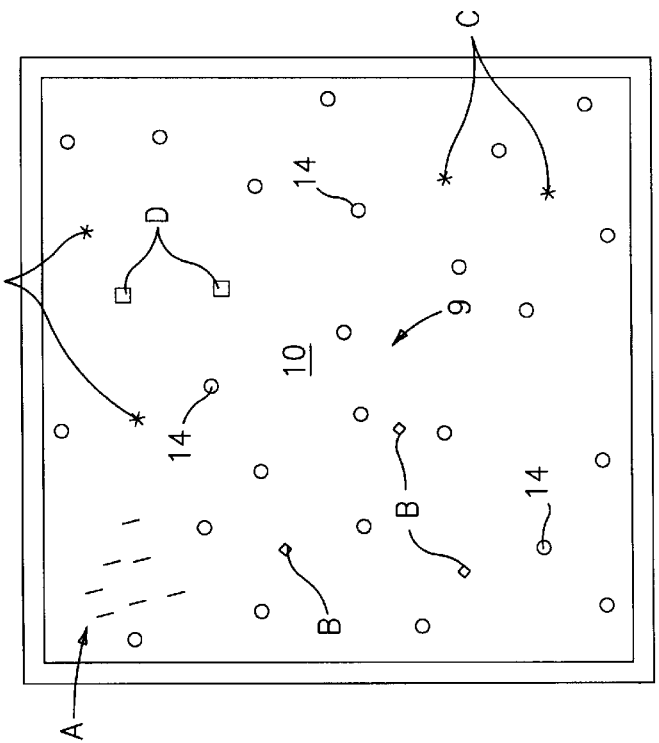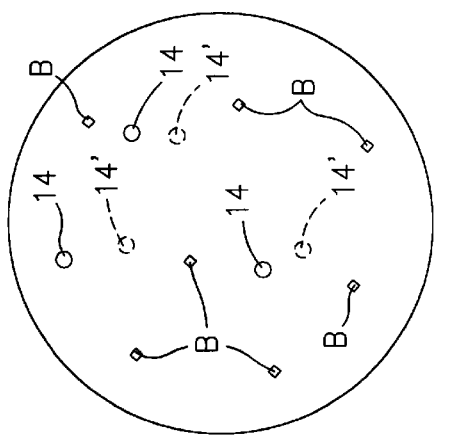

METHOD AND ASSEMBLY FOR SEPARATING FORMED CONSTITUENTS FROM A LIQUID CONSTITUENT IN A COMPLEX BIOLOGIC FLUID SAMPLE

TECHNICAL FIELD

This invention relates to an apparatus and method for separating formed constituents from the liquid constituent in a biologic fluid sample, so as to facilitate use of an optical instrument to examine the formed constitutes. More particularly, this invention relates to an apparatus and method which results in the formed constituents being disposed on a planar surface in the apparatus which planar surface conforms to the focal plane of the optical instrument.

BACKGROUND ART

Formed constituents in complex biologic fluid samples are typically isolated in, or separated from, the liquid constituent of the sample so as to enable detailed examination of the formed constituents. Flow cytometry is one technique for identifying formed constituents, such as blood cells in a blood sample. Using this technique, various types of blood cells and other formed constituents in blood can be differentiated from each other, and can be counted. In performing this procedure, the blood sample must be diluted prior to being passed through the flow cytometer. The aforesaid flow cytometry technique does not enable cells or other formed constituents in a blood sample to be quiescently examined. This technique cannot be efficiently used to detect rare events in a blood sample unless the sample is subject to enrichment procedures such as magnetic particle bead enrichment procedures of the type offered by Dynel of Norway.

A second technique for identifying and counting white blood cells and platelets in an anticoagulated whole blood sample is described in U.S. Pat. No. 4,027,660, and in other patents to Robert A. Levine and/or Stephen C. Wardlaw. This technique utilizes a capillary tube having an elongated insert disposed therein. The blood sample is admixed with a stain such as acridine orange, and centifuged in the capillary tube. The white cells and platelets settle out in the tube between the float and the tube wall so that the white blood cell and platelet layers are elongated by a factor of about ten. The elongation of the cell and platelet layers allows one to ascertain differential white cell and platelet counts in the tube by measuring the distance between opposite cell layer interfaces, and converting the measurements to cell counts. This second technique also does not enable the examination of individual blood cells in the blood sample.

U.S. Pat. No. 6,197,523 describes a method for analyzing a sample of anticoagulated whole blood for the presence or absence of abnormal epithelial cells and/or hematologic progenitor cells. The method involves placing the whole blood sample in a transparent sample tube which includes an insert that occupies sufficient volume in the sample tube so as to form a well defined annular area in the sample tube between the insert and the tube wherein individual cells will be isolated and can be examined. The well defined area of the sample tube is examined under magnification of at least 100X whereby individual cell morphology can be examined therein. As noted, the aforesaid method requires centrifugation of the whole blood sample in the sample tube before the isolated cell can be examined.

A multi-constituent fluid sample can be centrifuged so as to separate the liquid component of the sample from the formed constituents in the sample. This technique is most commonly used for urinalysis. In a biologic fluid sample containing cells or other particulates, the particulates will gravimetrically settle out separately from the liquid constituent, and the cells and particulates will also separate from each other according to their specific gravity. After the sample has been centrifuged, the liquid and the formed constituent fractions of the sample are separated from each other, and one or the other is further analyzed.

In the case of a urinalysis, upon completion of centrifugation, 90 to 95% of the supernatant liquid is decanted or discarded, and the cells and particulates are re-suspended in a smaller amount of the remaining liquid and placed in a chamber, or on a microscope slide for examination. It will be appreciated that the examination of various types of cells or particulates using the centrifugation technique is time-consuming and requires considerable skill on the part of the technician. This technique is also not precise due to the loss or destruction of sample components during centrifugation, and in the case of urinalysis, the imprecision of the decantation and re-suspension steps.

Formed constituents can also be separated from a biologic fluid sample by filtering. Using this technique, the fluid sample is forced to flow through a filter having a pore size which will prevent certain size formed constituents from passing therethrough. Thus if the size of a target formed constituent found in the sample is known, an appropriate filter can be selected for separating that target constituent from the sample. Once the formed constituents are trapped on the filter they can be removed and cultured, or further analyzed. Problems encountered with this technique include the cost of the various filters; the need to know the size of the target formed constituents; the plumbing required to focus the sample to flow through the filter; and the potential of filter clogging.

Formed constituents that may be isolated from solutions by centrifugation and/or filtering include; microbes in biologic fluids; casts in urine; somatic cells and blood cells in body fluids, other than blood; cysts; cells from cytological specimens obtained by brushing, aspiration, or scraping, which have been placed in a liquid medium; ova and parasites found in stool samples; and cancerous epithelial and hematologic progenitor cells from anticoagulated whole blood.

As noted above, known techniques for separating formed constituents from a liquid constituent in a biologic fluid sample all include centrifugation of the sample or filtering of the sample. It would be desirable to provide a technique for separating relatively rare formed constituents from a liquid constituent in a quiescent biologic fluid sample, which technique operates in a quiescent manner, is inexpensive, does not require the use of expensive adjunct paraphernalia such as centrifuges, fluid plumbing and filters, and does not require a high degree of expertise and experience to use.

DISCLOSURE OF THE INVENTION

This invention relates to a method and apparatus for use in separating formed constituents from a liquid constituent in an aqueous fluid sample mixture. Candidate aqueous sample mixtures include; urine; cerebrospinal fluid; pleural fluid-; ascites; fluids aspirated from cysts, such as thyroid and breast cysts cytologic specimens which have been placed in a fluid; aqueous suspensions of stool samples; platelet-rich plasma samples, prepared aqueous bacterial growth mixtures, and the like.

The apparatus of this invention includes a sample chamber which has a transparent sample-viewing portion, and which includes a planar expandable wall, capable of expanding in the presence of aqueous media; such wall being a hydrogel when expanded by addition of aqueous solutions in accordance with the instant invention. The medium, before expansion, may contain an amount of aqueous solution which is below the medium's equilibrium capacity thus rendering the medium capable of further hydration and expansion, or the medium may be a xero gel, i.,e., a dry polymeric structure that, upon absorption of water, becomes a hydrogel, swelling in the process. For the sake of simplicity, the term "hydrogel" as used in this application is intended to include any structured water swellable polymeric matrix from the dry state to the fully swollen equilibrium state. The hydrogel-layered wall is disposed opposite to the sample-viewing portion. The layer of the hydrogel has a constant thickness so that the surface of the hydrogel layer which is most proximal to the sample-viewing portion of the chamber is planar. When the apparatus is used to analyze a sample, the chamber is filled with an amount of the sample being examined, the sample being deposited on top of the hydrogel layer. The sample chamber has a known volume, and volume of the layer of the water-absorbent hydrogel is such that, when further hydrated, it will absorb essentially all of the water in the sample and substantially fill the sample chamber with the hydrogel.

After the fluid sample is added to the chamber, the hydrogel will expand toward the sample-viewing portion of the chamber until the chamber is substantially completely filled with the expanded hydrogel. The surface of the expanded hydrogel which is most proximal to the sample-viewing portion of the chamber will remain planar as the hydrogel layer swells. The aqueous constituent of the biologic sample will be absorbed into the hydrogel thereby causing expansion or swelling of the hydrogel. As the hydrogel expands, any formed constituents which are contained in the sample will be captured on the moving planar surface of the hydrogel and will remain in place on that surface of the hydrogel as the hydrogel continues to expand. When the hydrogel has reached its final expanded volume, substantially all of the liquid constituent in the sample will have been absorbed into the hydrogel and all of the formed constituents in the sample will have been captured on the surface of the hydrogel. Since the capture surface of the hydrogel remains planar, and is prefereably pressed against the sample-viewing portion of the chamber, the captured formed constituents in the sample will be fixed on a planar surface which can be made to occupy the focal plane of an instrument that is used to examine the captured formed constituents. The various formed constituents which are in the sample and which are captured on the surface of the rehydrated hydrogel can be differentially highlighted by analyte-specific agents so that various formed constituents can be differentiated from each other. Formed constituents can also be stained so that they can be morphologically examined on the hydrogel surface. Various differentially highlighted formed constituents can also be counted. Since the volume of sample added to the chamber is known, formed constituent counts per volume of sample can be derived. Isolation and concentration of formed constituents on the hydrogel surface also allows harvesting of specific formed constituents from the hydrogel surface for further analysis of the harvested constituents. The apparatus of this invention can be scanned by an optical scanning instrument, such as a microscope, or an optically differentiating instrument.

It is therefore an object of this invention to provide a method and apparatus for use in obtaining information relating to formed constituents contained a quiescent biological fluid sample.

It is an additional object of this invention to provide a method and apparatus of the character described wherein the formed constituents in the sample are captured on the planar surface of an expanded hydrogel disposed in a sample container.

It is another object of this invention to provide a method and apparatus of the character described wherein the liquid constituent in the sample is operative to expand a layer of a water-absorbent hydrogel disposed in the sample container.

It is a further object of this invention to provide a method and apparatus of the character described wherein the planar surface of the expanded hydrogel forms a focal plane for an optical examining instrument which is used in conjunction with the sample container.

It is yet another object of this invention to provide a method and apparatus of the character described wherein individual ones of the formed constituents can be harvested from the planar surface of the hydrogel after the latter has been expanded in the chamber.

It is a further object of this invention to provide a method and apparatus of the character described wherein the number and type of target constituents per unit volume of sample can be derived.

BRIEF DESCRIPTION OF THE DRAWINGS

These and other objects and advantages of this invention will become more readily apparent from the following detailed description of an embodiment of the invention when taken in conjunction with the accompanying drawings in which:

FIG. 1 is a schematic cross sectional view of a sample analyzing container which includes a sample-receiving chamber having a water-absorbent hydorgel component on a wall thereof;

FIG. 2 is a cross-sectional view of a container of the type shown in FIG. 1 wherein the hydrogel coating has been expanded so as to substantially fill the chamber;

FIG. 3 is a schematic plan view of the container of FIGS. 1 and 2 showing an array of formed constituents from the sample which are captured on the upper surface of the expanded hydrogel in the chamber; and FIG. 4 is a composite image of an initial field of view of the specimen in the sample chamber, and a subsequent image of the same field of view of the specimen.

DETAILED DESCRIPTION OF A SPECIFIC EMBODIMENT OF THE INVENTION

Referring now to the drawings, FIG. 1 is a schematic illustration of a sample container which is denoted generally by the numeral 2, which container 2 includes a chamber 4 that is defined by a side wall 6 and a planar bottom 8. A constant thickness layer of a preferably transparent or translucent hydrogel 9 is disposed on the bottom wall 8 of the chamber 4. A suitable hydrogel includes "PHYTA" gel, which is a hydrogel formed from glucuronic acid, rhamnose and glucose. It is clear and colorless, and thus is a good material for use in the detection of formed constituents. This hydrogel is the product of Sigma Diagnostics.

Other suitable hydrogels include: polyethylene oxide; poly(ethylene oxide-co-propylene oxide); poly(vinyl pyrrolidone); poly(vinyl alcohol); poly (acrylamide); poly (vinyl acetate); poly(acrylic acid) [in $Na^{+form}$]; poly(acrylic acid-co-acrylimide) [in Na⁺form]; poly(acrylic acid) [in Na⁺form]; poly(methacrylic acid) [in Na⁺form ]; poly(methacrylic acid-co-acrylate); [in Na⁺form]; poly(acrylonitrile-co-acrylamide); poly(hydroxyethyl acrylate); poly(hydroxymethyl methacrylate); and hydrophilic poly(urethanes).

The top surface 10 of the hydrogel layer 9 is planar, mirroring the planar bottom wall 8 of the chamber 4. The volume of the hydrogel layer 9 which is disposed in the chamber 4 is such that, when the hydrogel 9 absorbs water from a sample added to the chamber 4, it will substantially fill the chamber 4, and it will absorb essentially all of the water in the sample. The chamber 4 will preferably be provided with a transparent portion 12, that may take the form of a microscope cover slide, which provides a window through which the top surface 10 of the gel 9 is observed. A plurality of identifiable formed bodies 14 may be pre-positioned on the gel surface 10 and used to allow the optical instrument 16 to focus on the top surface 10 of the hydrogel 9 after the latter has been expanded, as shown in FIG. 2.

The formed bodies 14 perform three functions, one being to allow the optical instrument 16 to focus on the hydrogel surface 10; and a second being to confirm the location of the surface 10 when the instrument 16 does not sense any other formed constituents on the surface. In the latter case, the instrument 16 will record that the sample being analyzed does not contain any formed bodies. The third function of the formed bodies 14 is to serve as optical registration or navigation points. This function is useful wherein the sample analysis being performed requires that multiple areas of the chamber be repeatedly examined over a period of time. Since most analyzing instruments are not capable of exact re-location of a given point on the surface, but rather an approximate re-location, a map of the performed body positions in any particular field can be used to realign subsequent images of the same field so that successive comparative measurements in that field over a period of time may be performed.

FIG. 4 is illustrative the aforesaid realignment utility of the formed bodies 14. Note that FIG. 4 illustrates a particular field of view in which a number of formed constituents B are found. The field of view also includes three of the formed bodies 14 which happen to be arranged in a triangular pattern. This field of view will be imaged by the scanning instrument, and the X, Y coordinate location of this field view will be recorded by the instrument. Assuming that the instrument is programmed to return to this particular field of view for some reason, it will use the recorded X, Y coordinates to return to the field of view in question. When it returns to the field view in question, it will not be able to exactly reproduce the positions of the formed constituents B or the positions of the formed bodies 14, thus the positions of the formed bodies in the re-imaged field of view may be as indicated in phantom in FIG. 4, which positions are denoted by the numeral 14'. The instrument then compares the re-imaged formed body 14' positions with the original formed body 14 positions, and adjusts the re-image field of view with the original field of view by superimposing the re-imaged positions of the bodies 14' with the originally imaged positions of the bodies 14. In this matter, the bodies 14, and their positions in a field of view can be used to navigate back to the identical field of view image. It will be appreciated that the formed bodies 14 will be randomly distributed throughout the sample so that any pattern of formed bodies 14 seen in a particular field of view will be unique to that field of view. An instrument which may be used to examine the samples can be similar to the instrument shown and described in co-pending U.S. patent application U.S. Ser. No. 09/255,673, filed Feb. 23, 1999.

FIG. 3 illustrates a typical assortment of formed constituents which may be found in a urine sample which is analyzed in accordance with this invention. The focusing bodies 14 are shown in FIG. 3. Captured formed constituents such as bacteria A; red blood cells B; casts C; and crystals D, for example, might be seen on the surface 10 of the hydrogel 9. It will be appreciated that some individual constituents A, B, C or D can be deferentially stained or otherwise highlighted; supravital stains can be used in the sample so as to allow morphological examination of certain ones of the constituents; and individual constituents can be removed from the hydrogel surface 10 for further examination. Once a constituents is identified by the instrument 16, the exact location of the constituent will be known, and will not change, thus the constituent in question can be relocated.

One way that the sample chamber can be prepared for the sample analysis is as follows. An empty sample chamber can be filled with an at least partially hydrated hydrogel so that the upper surface of the hydrated hydrogel is planar, and is co-planar with the plane of the lower surface of the chamber 12. The thus-filled chamber assembly can then be subjected to an environment which will cause water to be evaporated from the hydrogel so as to shrink the hydrogel layer in the chamber and displace the upper surface of the hydrogel component downwardly away from the lower surface of the cover 12. An aliquot of an aqueous-based sample to be analyzed for formed constituents is then introduced into the sample chamber onto the shrunken hydrogel component, and the latter is then allowed to expand back to its original volume through absorption of water from the sample. The upper surface of the re-expanded gel component is thus thrust against the cover 12 so as to move any trapped formed components in the sample into a focal plane which coincides with the lower surface of the cover 12. Before adding the sample to the shrunken gel, the formed bodies 14 can be placed on the upper surface of the shrunken gel.

Another method which could be used to produce the sample chambers is a follows. When "soft" (i.,e., partially hydrated) hydrogels used as the water absorbent, these soft gels might not be partially dehydrated in situ in the sample chamber. They could be pre-prepared outside of the sample chamber. For example, one could cut gel discs from a gel sheet and place the cut discs in the bottom of the chamber so that they would adhere to the chamber bottom. In any case, the gel must be able to absorb essentially all of the water in the sample, and must not be able to lift the cover 12 away from the chamber when the gel is expanded.

It will be appreciated that the method and apparatus of this invention provide an inexpensive technique for examining certain biologic fluid samples for formed constituents. Dissimilar formed constituents which may be found in the sample can be differentiated from each other, can be harvested from the apparatus, and can be counted. The formed constituents in the sample are separated from the liquid constituent of the sample by causing the liquid constituent to be absorbed by a hydrophilic hydrogel which is not in its aqueous equilibrium state so as to further hydrate the hydrogel. During further hydration of the hydrogel, any formed constituents in the sample will be captured on the expanded surface on the hydrogel.

Since many changes and variations of the disclosed embodiment of the invention may be made without departing from the inventive concept, it is not intended to limit the invention otherwise than as required by the appended claims.

What is claimed is:

1. A method of examining characteristics of at least one formed constituent which is contained in an aqueous-based biologic fluid sample, said method comprising:

a) the step of providing a sample container which includes a sample chamber having a known volume, said chamber being defined by a first wall, side walls, and a transparent sample-viewing portion, which sample-viewing portion is disposed opposite to said first wall; said chamber further including a layer of an expendable hydrogel disposed on said chamber first wall, said expandable hydrogel layer having a planar surface which faces said sample-viewing portion of said chamber, and said expandable hydrogel layer having a volume which will cause said hydrogel to essentially fill said chamber when said hydrogel layer is expanded as a result of absorbing essentially all of the aqueous constituent of the sample;

b) the step of introducing the fluid sample into said chamber on said hydrogel layer, and allowing the aqueous constituent of said fluid sample to be absorbed by and expand said hydrogel layer, while capturing formed constituents from said fluid sample on a surface of said expanding hydrogel layer in said chamber; and c) examining at least one of the formed constituents which is captured on the surface of the expanded hydrogel layer in the chamber.

2. The method claim 1 wherein said surface of said hydrogel layer is planar and remains planar while said hydrogel layer is expanded.

3. The method claim 2 wherein said planar surface includes optically distinguishable formed bodies disposed thereon which allow confirmation of the position of said planar surface after said hydrogel layer has been expanded.

4. A method for separating at least one formed constituent from an aqueous-based complex biologic fluid sample, said method comprising:

a) the step of providing a sample container which includes a sample chamber having a known volume, said chamber being defined by a bottom wall, side walls, and a transparent sample-viewing wall, which sample-viewing wall is disposed opposite to said bottom wall; said chamber further including a layer of an expandable hydrogel disposed on said chamber bottom walls, said hydrogel layer having a planar surface which faces said sample-viewing wall of said chamber, and said hydrogel layer being operable is essentially fill said chamber when said hyrdogel layer is expanded as a result of absorbing essentially all of the aqueous constituent of the fluid sample; and b) the step of introducing the fluid sample into said chamber on said hydrogel layer, and allowing the aqueous constituent of said fluid sample to be absorbed into and expand said hydrogel layer while capturing at least one constituent from said fluid sample on a surface of said expanded hydrogel layer in said chamber.

5. A method for locating an upper surface of an expanded transparent or translucent hydrogel in a sample chamber, said method comprising:

a) the step of providing a sample container which includes a sample chamber, said chamber being defined by a first wall, a side wall, and a transparent sample-viewing wall, which sample-viewing wall is disposed opposite to said first wall; said chamber further including an expandable layer of a transparent or translucent hydrogel disposed on said chamber first wall, said hydrogel layer having a planar surface which faces said sample-viewing wall of said chamber;

b) the step of expanding said hydrogel layer so as to move said planar surface of said hydrogel layer to a final location in said chamber; and c) the step of positioning optically distinguishable formed bodies in said chamber, which bodies are coplanar with said final location of said planar surface so that an optical instrument can focus on said bodies and thereby locate the position of said final location of said planar surface of the hydrogel in the chamber.

6. The method of claim 5 wherein said formed bodies are positioned on said planar surface of said hydrogel prior to expansion of said hydrogel, and wherein said formed bodies are carried to said final location of said planar surface as said hydrogel is expanded.

* * * * *